(12) United States Patent
Tiitta et al.

(10) Patent No.: US 7,604,794 B2
(45) Date of Patent: Oct. 20, 2009

(54) ZEOLITE CATALYST FOR SKELETAL ISOMERISATION OF OLEFINS

(75) Inventors: Marja Tiitta, Porvoo (FI); Elina Harlin, Vantaa (FI); Jaana Makkonen, Söderkulla (FI); Narendra Kumar, Turku (FI); Dmitry Yu Murzin, Turku (FI); Tapio Salmi, Turku (FI)

(73) Assignee: Neste Oil Oyj, Espoo (FI)

( * ) Notice: Subject to any disclaimer, the term of this patent is extended or adjusted under 35 U.S.C. 154(b) by 267 days.

(21) Appl. No.: 10/549,169

(22) PCT Filed: Mar. 9, 2004

(86) PCT No.: PCT/FI2004/000127

§ 371 (c)(1),
(2), (4) Date: Jul. 3, 2006

(87) PCT Pub. No.: WO2004/080590

PCT Pub. Date: Sep. 23, 2004

(65) Prior Publication Data

US 2006/0275207 A1    Dec. 7, 2006

(30) Foreign Application Priority Data

Mar. 14, 2003   (FI) ................................. 20030383

(51) Int. Cl.
C01B 39/04 (2006.01)
C01B 39/48 (2006.01)
C07C 5/27 (2006.01)

(52) U.S. Cl. ....................... 423/705; 423/706; 423/707; 423/718; 423/711; 585/671

(58) Field of Classification Search .................... None
See application file for complete search history.

(56) References Cited

U.S. PATENT DOCUMENTS 3,702,886 A    11/1972  Argauer et al.

(Continued)

FOREIGN PATENT DOCUMENTS

EP    0 347 273 A1    12/1989

(Continued)

OTHER PUBLICATIONS

Journal of Catalysis, vol. 150, 1994, Wen-Qing Xu et al., pp. 34-45.

(Continued)

Primary Examiner—Melvin C Mayes
Assistant Examiner—James Corno
(74) Attorney, Agent, or Firm—Birch, Stewart, Kolasch & Birch, LLP

(57) ABSTRACT

The present invention relates to an active and selective zeolite catalyst having MTT structure that is useful in skeletal isomerisation of light olefins. The method for the manufacture of the zeolite catalyst having MTT structure comprises the steps of a) preparing of a gel mixture capable of forming crystalline material, and the mixture comprising sources of alkali or alkaline earth metal (M), of an oxide of a trivalent element (X), of an oxide of a tetravalent element (Y), water and a directing agent (R), and the mixture having a composition, in terms of molar ratios, within the given ranges; b) maintaining the mixture under sufficient conditions, including a temperature of from about 100° C. to about 250° C., under dynamic mode of stirring until crystals of the material are formed, recovering the material; and c) removing the directing agent (R) partly or totally with a calcination procedure.

14 Claims, 4 Drawing Sheets

U.S. PATENT DOCUMENTS

Figure 1:
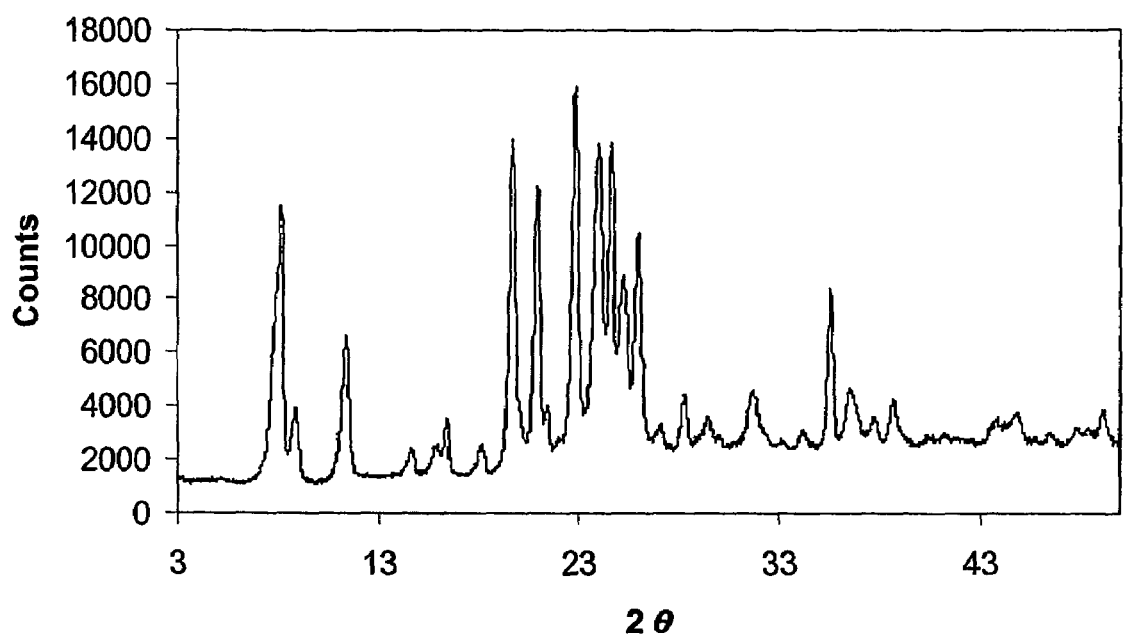

| | | |
|---|---|---|
| 3,926,782 A | 12/1975 | Plank et al. |
| 4,016,245 A | 4/1977 | Plank et al. |
| 4,076,842 A | 2/1978 | Plank et al. |
| 4,104,151 A | 8/1978 | Rubin et al. |
| 4,481,177 A | 11/1984 | Valyocsik |
| 4,490,342 A | 12/1984 | Valyocsik |
| 4,531,012 A | 7/1985 | Valyocsik |
| 4,619,820 A | 10/1986 | Valyocsik |
| 5,157,194 A | 10/1992 | Rahmim et al. |
| 5,237,121 A | 8/1993 | Rahmim et al. |
| 5,243,090 A | 9/1993 | Haag et al. |
| 5,332,566 A | 7/1994 | Moini |
| 5,449,851 A | 9/1995 | Rahmin et al. |
| 5,489,726 A * | 2/1996 | Huss et al. .................. 585/671 |
| 5,491,296 A | 2/1996 | Bergemann |
| 5,510,560 A | 4/1996 | O'Young et al. |
| 5,817,907 A | 10/1998 | Benazzi et al. |
| 6,045,688 A | 4/2000 | Ruottu et al. |
| 6,099,820 A | 8/2000 | Miller |
| 6,111,160 A | 8/2000 | Powers et al. |
| 6,323,384 B1 | 11/2001 | Powers et al. |
| 2004/0049092 A1 | 3/2004 | Nikkonen et al. |

FOREIGN PATENT DOCUMENTS

| | | |
|---|---|---|
| EP | 0 523 838 A2 | 1/1993 |
| EP | 0 549 294 A1 | 6/1993 |
| EP | 0 574 994 A1 | 12/1993 |
| FI | 101156 B | 4/1998 |
| FI | 20002783 A | 6/2002 |
| GB | 2 190 910 A | 12/1987 |
| GB | 2 202 838 A | 10/1988 |
| WO | WO-94/08920 A1 | 4/1994 |
| WO | WO-96/29285 A1 | 9/1996 |
| WO | WO-96/29286 A1 | 9/1996 |

OTHER PUBLICATIONS

MTT, ZSM-23, Ernst, S., Retrieved on Aug. 21, 2002, Retrieved from the Internet: <URL:http://www.isa-synthesis.org/Recipes/ZSM-23.html>.

Rollmann et al., J. Phys. Chem. B, vol. 103, No. 34, pp. 7175-7183, 1999.

Giordano et al., Stud. Surf. Sci. Cat. 84 (1994) pp. 141-146.

Moini, et al., Stud. Surf. Sci. Cat. 84 (1994), pp. 23-28.

Kumar et al., Applied Catalysis A: General 235 (2002) pp. 113-123.

van Donk et al., Applied Catalysis A: General 212 (2001) pp. 97-116.

* cited by examiner

ZEOLITE CATALYST FOR SKELETAL ISOMERISATION OF OLEFINS

FIELD OF INVENTION

The present invention relates to an active zeolite catalyst having MTT structure and to a method for the manufacture of said catalyst. More particularly, the invention relates to a method for preparing the MTT structure whereby the synthesis is facilitated and reproducible, and the obtained product exhibits high catalytic utility. Said zeolite catalyst is particularly suitable for olefin isomerization reactions.

BACKGROUND OF INVENTION

Molecular sieves are an important class of inorganic materials used in catalysis. Zeolites are an essential group of molecular sieves. Zeolites are crystalline aluminosilicates with a well-defined pore structure. The International Zeolite Association recognized 136 different groups of framework in January 2003. MTT is one of the structural groups of zeolites.

Four types of zeolites having MTT structure are known in the art: ZSM-23, EU-13, ISI-4 and KZ-1. ZSM-23 zeolite has one-dimensional 10-ring channels. The unit cell of ZSM-23 can be represented as: $Na^+_n [Al_n Si_{24-n} O_{48}]\sim 4H_2O$, n<2. The dimensions of the channel system are 0.45×0.52 nm [1].

In general, various zeolites are prepared using hydrothermal synthesis. In principal three major variables influence on the zeolite structure crystallised and said variables are the composition of the reaction mixture, the template and the time. For example, U.S. Pat. No. 3,702,886 and U.S. Pat. No. 3,926,782 describe the synthesis of MFI-structure based zeolite ZSM-5, U.S. Pat. No. 4,481,177 describes the synthesis of TON structure based zeolite ZSM-22, and U.S. Pat. No. 4,016,245 describes the synthesis of FER structure based zeolite ZSM-35.

Several publications describe different factors, which are important in zeolite synthesis. Rollmann et al. teaches about the role of small amines in zeolite synthesis [2]. The synthesis of high-silica zeolites with one-directional medium pore systems, by using nitrogen-free templates has been studied by Giordan et al. [3]. Moini et al. [4] describe the role of diquaternary cations as directing agents in zeolite synthesis. The present inventors have studied in detail the effect of synthesis time and mode of stirring on physicochemical and catalytic properties of ZSM-5 zeolite catalysts [5].

Several methods for preparation of Me-structures are known. U.S. Pat. No. 4,076,842, U.S. Pat. No. 4,104,151, GB 21 90910, GB 2 202 838, U.S. Pat. No. 4,490,342, U.S. Pat. No. 4,531,012 and U.S. Pat. No. 4,619,820 describe the synthesis of ZSM-23 from reaction mixtures containing different amines as structure directing agents or templates. International patent applications WO 96/29285 and WO 96/29286 provide methods for the production of medium pore zeolites, including ZSM-23, in the absence of any nitrogen-containing templating agent other than the small neutral amine. U.S. Pat. No. 5,332,566 teaches the formation of ZSM-23 with a templating agent having the formula $C_{14}H_{36}N_3^{3+}$. U.S. Pat. No. 6,099,820 discloses a method for making MTT zeolites without an organic template. EP 0 347 273 provides a method for the manufacture of a MTT type zeolite using fluorine containing compounds in the synthesis mixture.

Isomerization is a hydrocarbon transformation reaction and it is catalyzed by acid sites. In an isomerization reaction, the molecular formula of one substance does not change but its structure changes. Isomerization can be divided into several groups after the group of molecules that are isomerized (paraffin isomerization, olefin isomerization, etc.), or alternatively it can also be divided after the reaction type (skeletal isomerization, double-bond isomerization, etc.).

The term "skeletal isomerization" stands here for a reaction wherein one n-olefin reacts to a corresponding isoolefin. This reaction is also known as olefin isomerization, hydrocarbon conversion, preparation of branched olefins, conversion of normal olefins to branched olefins and structural isomerization.

Several patents describe skeletal isomerization of olefins with zeolite catalysts. For example, in patents EP 0574 994, EP 0 523 838, U.S. Pat. No. 5,491,296, U.S. Pat. No. 5,510, 560, U.S. Pat. No. 6,323,384 and U.S. Pat. No. 6,111,160 ferrierites are used in skeletal isomererization. ZSM-35 has a similar type of zeolite structure as ferrierite and its use in skeletal isomerization is discussed in U.S. Pat. No. 5,449,851 and WO 94/08920.

Other potential catalysts for skeletal isomerization of olefins are catalysts based on TON structure like ZSM-22. In U.S. Pat. No. 5,157,194, U.S. Pat. No. 5,237,121 and EP 0 5 49 294 the use of ZSM-22 based catalysts in skeletal isomerization is described.

MTT structure based catalysts, such as ZSM-23, are also used in skeletal isomerization of light olefins. In an example of U.S. Pat. No. 5,243,090, HZSM-23 is used in n-butene conversion under a pressure of 720 kPa and at temperatures between 551-554° C. The conversion of n-butene was 38% with 84% selectivity to isobutene. In U.S. Pat. No. 5,817,907, in examples 3 and 4, the uses of fresh and coked ZSM-23 catalysts in skeletal isomerization of n-butene are shown. The conversion of n-butene with the coked catalyst was 46% with 40% isobutene selectivity, and with the fresh catalyst, 52% with 20% isobutene selectivity, respectively.

Recently, a summary of the performance of different zeolite catalysts used in the skeletal isomerization has been presented [6]. It was found that ZSM-5, ZSM-22 and ZSM-23 are less adequate for butene skeletal isomerizarion than ferrierite, due to structural characteristics and a less suitable acidity (Table 1). All the studied zeolite catalysts showed a limited activity to isoolefins and a fast deactivation in the olefin skeletal isomerization reaction.

TABLE 1

Microporous catalysts and their properties in butene skeletal isomerization [6]

| Catalyst | Si/Al ratio | n-$C_4^{2=}$ Conversion (%) | i-$C_4^{2=}$ Selectivity(%) | TOS-max (h) |
|---|---|---|---|---|
| Ferrierite | 57 | 50 | 90 | 1200 |
| ZSM-5 | 27 | 55 | 25 | 1 |
| ZSM-22 | 26 | 87 | 36 | 71 |
| ZSM-22 | 53 | 28 | 80 | 5 |
| ZSM-23 | 60 | 45 | 65 | 20 |
| SAPO-11 | Al/Si = 11.2 | 56 | 65 | 2 |
| CoAPO-11 | Al/Co = 75 | 39 | 98 | 24 |

In the light of the state of the art it can be seen that there is an evident need for a highly active and selective zeolite catalyst, which can be used in olefin isomerization reactions.

OBJECT OF THE INVENTION

An object of the invention is to provide a method for the manufacture of an active and selective zeolite catalyst having MT structure.

A further objective of the invention is to provide a novel, active and selective zeolite catalyst having MTT structure.

A further object of the invention is the use of the active and selective zeolite catalyst having MTT structure, particularly in olefin isomerization reactions.

Characteristic features of the method for the manufacture of the active and selective zeolite catalyst having MTT structure, of the active and selective zeolite catalyst having MTT structure, and the use of the active and selective zeolite catalyst having MTT structure are provided in the claims.

SUMMARY OF THE INVENTION

It has now been found that the problems related to zeolite catalysts, which are used in olefin isomerization reactions, can be avoided or at least significantly decreased by the active and selective zeolite catalyst having MTT structure, prepared according to the invention.

The MTT structure based catalyst comprises a carrier selected from alumina, silica or clay or any other carrier of the state of the art and possible combinations thereof. The amount of carrier varies between 10-90 wt-%, calculated on the total weight of the catalyst.

The method for the manufacture of the novel zeolite catalyst having MTT structure comprises the following steps:
a) Preparation of a gel mixture using a gel ripening pre-treatment step at ambient temperature,
b) Hydrothermal synthesis in dynamic mode of stirring ("rotational" or "vigorous internal" stirring), and
c) Removing of structure directing agent from the zeolite catalyst using a calcination procedure.

The phase pure and highly crystalline zeolite catalysts having MTT structure, which are prepared according to the method of the invention, have superior selectivity and activity, particularly in skeletal isomerization of light olefins. Said catalysts provide essentially higher yields of isoolefins than the currently available catalysts according to the state of the art, presented in Table 1.

DETAILED DESCRIPTION OF THE INVENTION

Without wishing to be restricted by the following explanations and theoretical considerations regarding the synthesis of the novel zeolite catalysts with MTT structure, which are particularly suitable for olefin isomerization reactions, the essential features of the invention are discussed as follows.

The method for the manufacture of a zeolite catalyst having MTT structure comprises:
a) Preparing of a gel mixture capable of forming crystalline material, and said mixture comprising a source(s) of alkali or alkaline earth metal (M) selected from sodium, potassium, magnesium, calcium, a source(s) of an oxide of a trivalent element (X) selected from aluminium and gallium, a source(s) of an oxide of a tetravalent element (Y) selected from silicon and germanium, water and a directing agent (R) selected from compounds comprising organic nitrogen containing cations, preferably pyrrolidine and diethanolamine, and said mixture having a composition, in terms of molar ratios, within the following ranges of Table 2, wherein (O) is oxygen and (H) hydrogen;

TABLE 2

| Molar ratio | Range |
|---|---|
| $YO_2/X_2O_3$ | 30 to 300 |
| $H_2O/YO_2$ | 20 to 100 |
| $OH^-/YO_2$ | 0.1 to 0.4 |

TABLE 2-continued

| Molar ratio | Range |
|---|---|
| $M/YO_2$ | 0.05 to 1.0 |
| $R/YO_2$ | 0.02 to 1.0 | b) Carrying out hydrothermal synthesis wherein said mixture from step a) is maintained under sufficient conditions including a temperature from about 100° C. to about 250° C. under dynamic mode of stirring until crystals of said material are formed, recovering the material, and
c) Removing of said directing agent (R) partly or totally from the material obtained in step b) with a calcination procedure, whereby a zeolite catalyst having MTT structure is obtained.

A typical X-ray diffraction (XRD) pattern of a zeolite catalyst with MTT structure according to the invention is presented in FIG. 1. No other zeolite as an impurity was observed. The X-ray diffraction pattern was collected with Siemens Daco-MP Kristalloflex instrument. The sample holder was made of PVC.

Figure 2:
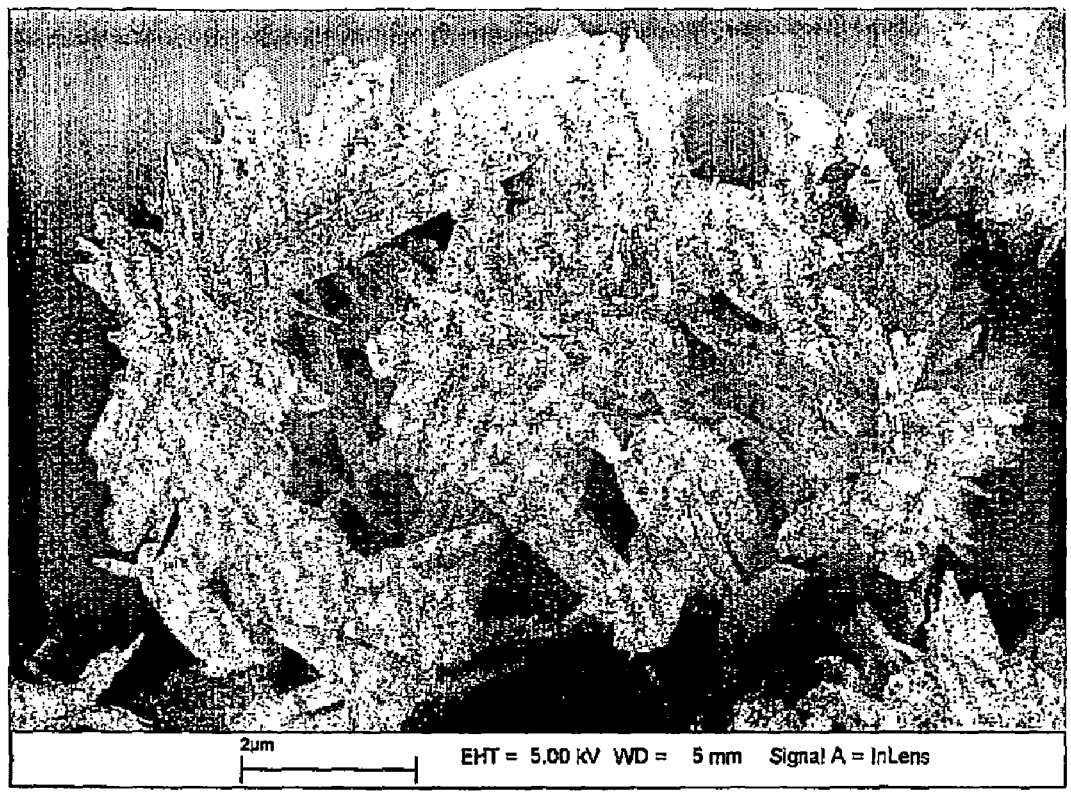

FIG. 2, a scanning electron micrograph of a zeolite catalyst with MTT structure according to the invention, shows that the zeolite catalyst comprises small rod shaped crystals.

The method for the manufacture of the zeolite catalyst having MTT structure, preferably comprises the following steps:
a) Preparation of the gel mixture using a gel ripening pre-treatment step at ambient temperature,
b) Carrying out the hydrothermal synthesis in dynamic mode of stirring ("rotational" or "vigorous internal" stirring), and
c) Removing of the structure directing agent (R) partly or totally from the zeolite catalyst using a calcination procedure.

The steps a), b) and c) are described in detail in the following:

Step a): The preparation of a gel mixture using a gel ripening pre-treatment step is carried out as follows: Solution A is prepared by adding a source(s) of an oxide of an alkali or alkaline earth metal selected from sodium, potassium, magnesium and calcium, preferably sodium hydroxide, potassium hydroxide or sodium carbonate, to water, preferably ion exchanged or distilled water, and the obtained solution is stirred.

A source(s) of an oxide of a tetravalent element selected from silicon and germanium, preferably colloidal silica, solid silica, fumed silica or silica hydroxide, is added to the above described Solution A with continuous stirring. After the addition of the oxide of the tetravalent element, the mixture is further stirred. This obtained mixture is denoted as Solution B.

Solution C is prepared by adding a source(s) of an oxide of a trivalent element selected from aluminium and gallium, preferably aluminium sulphate $(Al_2(SO_4)_3 \cdot 18H_2O)$, hydrated aluminium hydroxides, aluminates, aluminium isoproxide and alumina, to water, preferably deionized or distilled water, and the mixture is further stirred. To this mixture, a directing agent (R) selected from compounds comprising organic nitrogen containing cations, preferably pyrrolidine or diethanolamine, is added, preferably dropwise, with vigorous stirring. After the addition of the directing agent, the mixture is further stirred.

Solution C is added to Solution B slowly. After the addition of Solution C to Solution B, the obtained gel mixture is further stirred (gel ripening). To this gel mixture sulphuric acid is added slowly, keeping pH in an alkaline range, preferably in the range of 8.5-13.5. The gel mixture is further stirred (gel ripening).

The use of gel ripening (gel ageing) provides nuclei necessary for the synthesis of comparatively uniform shape, size and distribution of the crystals of the zeolite having MTT structure. Gel ripening may also shorten the synthesis time (i.e. it can accelerate the crystallization process). Further, it may influence the yield of the zeolite with MTT structure and influence the Si/Al ratio.

Step b): The hydrothermal synthesis in dynamic mode of stirring ("rotational" or "vigorous internal" stirring) is carried out as follows: The gel mixture prepared in step a) is charged into a reactor, which is optionally pressurized to a pressure between 0.2-5 Mpa. The strirring is started and the temperature of the reactor is raised to a temperature suitable for the crystallization, preferably to 100-250° C. and particularly preferably to 120-220° C. The synthesis is carried out in a dynamic mode. The hydrothermal synthesis can be carried out in a heatable, stirred tank reactor, in a loop reactor, in an ebullated reactor or in any other reactor suitable for solid-liquid phase reactions known in the state of the art.

After the completion of the synthesis, the temperature of the reactor is decreased rapidly. The product is isolated, washed with water, preferably deionised or distilled water, and dried.

The hydrothermal synthesis is carried out in a dynamic mode (i.e. rotation or vigorous internal stirring during synthesis). This mode of stirring is known from the state of the art to influence phase purity and size of crystals of aluminosilicate type of zeolites, and if static mode i.e. without stirring is used, larger crystals are obtained when compared with preparation under continuous stirring. The use of dynamic mode of stirring in the synthesis of the zeolite with MTT structure results in zeolitic material with high crystallinity, phase purity and crystals with regular size.

Step c): Removal of the structure directing agent from the zeolite catalyst is carried out using a calcination procedure as follows:

The calcination procedure is performed by raising the temperature of an oven or other suitable heatable equipment containing the zeolite obtained from step b) with a slow heating rate, preferably 0.05-2° C./min to a temperature of 400-600° C. Preferably a slow heating rate is applied to reach an intermediate temperature of 200-400° C., which is then followed by raising the temperature to the final calcination temperature of 400-600° C.

The removal of the structure directing agent i.e. the organic template, is carried out by the calcination procedure. The removal of the structure directing agent after the completion of the synthesis of the zeolite catalyst is an important step in order to free its pores of organic compounds to obtain high surface area. Temperature, heating rate, duration of calcinations and presence of carrier gas during organic template removal from MTT structure may influence surface area, pore systems, location of framework alumina and formation of extra framework alumina.

The method optionally comprises replacing ions of the crystalline material, at least in part, by ion exchange with an ion or a mixture of ions selected from the group consisting of hydrogen and hydrogen precursors or metals.

The zeolite catalyst having MTT structure contains a carrier selected from alumina, silica or clay or any other carrier of the state of the art and possible combinations thereof. The amount of the carrier varies between 10-90 wt-%, calculated on the amount of the catalyst.

The catalyst can be formulated with techniques known in the art, such as spray drying, extrusion and the like.

The zeolite catalyst having MTT structure according to the invention can be modified using any conventional methods known in the art. Examples of such methods are calcination procedures, ion exchange procedures, impregnation procedures and various other treatments known in the art.

The different steps in the manufacture of the catalyst according to the invention can be performed in any suitable equipment generally known in the art.

The novel zeolite catalysts having MTT structure showed surprisingly high activities and selectivities, particularly in skeletal isomerization of light olefins. Additionally, no deactivation was observed in conditions where commercial catalysts were rapidly deactivated, as can be seen from Example 9.

The zeolite catalyst having MTT structure may be used in skeletal isomerization processes of olefins, suitably in fixed bed reactors and in fluidized bed reactors. In the process, a feed containing at least one group of olefins having 4 to 20, preferably from 4 to 10 carbon atoms, is brought into contact with the catalyst at a temperature between 50° C. and 500° C., depending on the olefin which is isomerized, and under a pressure between 0.01 and 5 MPa. Particularly suitable feed comprises $C_4$, $C_5$, $C_6$ or $C_7$ olefinic hydrocarbons, or mixtures thereof, preferably $C_4$, $C_5$ or $C_6$ olefinic hydrocarbons.

The isomerization process can be carried out in a packed bed reactor, a fixed bed reactor, fluidized bed reactor or a moving bed reactor. Especially preferred reactor system is described in FI patent 101156 and patent application FI20002783, the contents of which are incorporated by reference herein.

The invention is illustrated in detail with the following examples. However, the scope of the invention is not meant to be limited to the examples.

EXAMPLES

Example 1

Preparation of a Zeolite Catalyst Having MTT Structure

Step a): Solution A was prepared by adding 8.9 g of sodium hydroxide to 392 g of distilled water and stirred. 33.5 g of fumed silica was added to Solution A with continuous stirring. After the addition of the fumed silica, the solution was further stirred. This mixture was denoted as Solution B. Solution C was prepared by adding 3.9 g of aluminium sulphate (($Al_2(SO_4)_3 \cdot 18H_2O$)) to 49.2 g of distilled water and the mixture was further stirred. To this mixture, 17.9 g of pyrrolidine was added dropwise with vigorous stirring speed. After the addition of pyrrolidine, the mixture was further stirred.

Solution C was added slowly to Solution B. After the addition of Solution C to Solution B, the gel mixture was further stirred (gel ripening). To this gel mixture 8.0 g of sulphuric acid was added slowly. The prepared gel mixture was further stirred (gel ripening).

Step b): The prepared gel mixture was put in two teflon cups inserted in 300 ml steel autoclaves. The autoclaves were mounted over a shaft in an oven and the temperature of the oven was raised to 180° C. The synthesis was carried out in dynamic mode for 48 hours at 180° C. After the completion of the synthesis the autoclaves were quenched. The product was mixed with distilled water, filtered and washed with on-line flowing distilled water. The product was left to dry over a filter paper. The crystalline product was separated from the filter paper and dried over a ceramic dish in an oven with airflow. The temperature and time of drying were 110° C. for 12 h, respectively.

Step c): The calcination procedure was performed stepwise by raising the temperature of the muffle oven containing the zeolite sample (slow heating rate) to an intermediate temperature. The calcination was carried out at the intermediate temperature for an interval of time, followed by raising the temperature (slow heating rate) to the final calcination temperature below 600° C. where the zeolite was calcined.

The properties of the obtained product were the following: The Si/Al-ratio was 42, the amount of Brönsted acid sites was 90 μmol/g, the sodium content was 0.1 wt-%, the carbon content was 0.7 wt-% and the BET-surface area was 110 m²/g. The XRD-diffraction pattern is given in Table 3.

TABLE 3

XRD-diffraction pattern

| D/n | Intensity $I/I_0$ |
|---|---|
| 10.8 | 42 |
| 9.95 | 16 |
| 7.77 | 37 |
| 4.507 | 90 |
| 4.241 | 79 |
| 3.88 | 100 |
| 3.704 | 80 |

Example 2

Ion-Exchange Procedure

The sodium form of the zeolite catalyst having MTT structure, obtained from example 1, was transformed to proton form by repeated ion-exchange method using aqueous solutions of ammonium chloride. After the ion-exchange procedure, the ammonium form of the zeolite was washed thoroughly with distilled water. The ammonium form of the zeolite was dried at 100° C. for 10 h and it was transformed into proton form using the stepwise calcination procedure. The properties of the obtained product (New catalyst A) were the following: The Si/Al-ratio was 42, the amount of Brönsted acid sites was 170 μmol/g and the sodium content was 92 ppm.

Example 3

Preparation of a Zeolite Catalyst Having MTT Structure

Step a): Solution A was prepared by adding 8.9 g of sodium hydroxide to 392 g of distilled water and the mixture was stirred. 33.5 g of fumed silica was added to Solution A with continuous stirring. After the addition of fumed silica, the solution was further stirred. This mixture was denoted as Solution B. Solution C was prepared by adding 3.9 g of aluminium sulphate ($Al_2(SO_4)_3.18H_2O$) to 49.2 g of distilled water and the mixture was further stirred. To this mixture, 17.9 g of pyrrolidine was added dropwise with vigorous stirring speed. After the addition of pyrrolidine, the mixture was further stirred.

Solution C was added slowly to Solution B. After the addition of Solution C to Solution B, the gel mixture was further stirred (gel ripening). To this gel mixture 8.0 g of sulphuric acid was added slowly. The prepared gel mixture was further stirred (gel ripening).

Step b): The prepared gel mixture was put in two teflon cups inserted in 300 ml steel autoclaves. The autoclaves were mounted over a shaft in an oven and the temperature of the oven was raised to 180° C. The synthesis was carried out in dynamic mode at 180° C. for 24 h.

After the completion of the synthesis, the autoclaves were quenched. The product was mixed with distilled water, filtered and washed with on-line flowing distilled water. The product was left to dry over a filter paper. The crystalline product was separated from the filter paper and dried over a ceramic dish in an oven with airflow. The temperature and time of drying were 110° C. for 12 h, respectively.

Step c): The calcination procedure was performed stepwise by raising the temperature of the muffle oven containing the zeolite sample (slow heating rate) to an intermediate temperature. The calcination was carried out at the intermediate temperature for an interval of time, followed by raising the temperature (slow heating rate) to the final calcination temperature below 600° C. where the zeolite was calcined.

Example 4

Ion-Exchange Procedure

The sodium form of the zeolite catalyst having MTT structure, obtained from example 3, was transformed to proton form by a repeated ion-exchange method using aqueous solutions of ammonium nitrate. After the ion-exchange procedure, the ammonium form of the zeolite was washed thoroughly with distilled water. The ammonium form of zeolite was dried at 100° C. for 10 h and it was transformed into proton form by calcination.

Example 5

Preparation of a Zeolite Catalyst Having MTT Structure

Step a): Solution A was prepared by adding 8.9 g of sodium hydroxide to 392 g of distilled water and the mixture was stirred. 33.5 g of fumed silica was added to Solution A with continuous stirring. After the addition of fumed silica, the solution was further stirred. This mixture was denoted as Solution B. Solution C was prepared by adding 3.9 g of aluminium sulphate ($Al_2(SO_4)_3.18H_2O$) to 49.2 g of distilled water and the mixture was further stirred. To this mixture, 17.9 g of pyrrolidine was added with vigorous stirring speed. After the addition of pyrrolidine, the mixture was further stirred.

Solution C was added to Solution B slowly. After the addition of the Solution C to Solution B, the gel mixture was further stirred (gel ripening). To this gel mixture 8.0 g of sulphuric acid was added slowly. The prepared gel mixture was further stirred (gel ripening).

Step b): The prepared gel mixture was put in two teflon cups inserted in 300 ml steel autoclaves. The autoclaves were mounted over a shaft in an oven and the temperature of the oven was raised to 180° C. The synthesis was carried out in dynamic mode at 180° C. for 96 h. After the completion of the synthesis, the autoclaves were quenched. The product was mixed with distilled water, filtered and washed with on-line flowing distilled water. The product was left to dry over a filter paper. The crystalline product was separated from the filter paper and dried over a ceramic dish in an oven with airflow. The temperature and time of drying were 110° C. for 12 h, respectively.

Step c): The step calcination procedure was performed by raising the temperature of the muffle oven containing the zeolite sample (slow heating rate) to an intermediate temperature. The calcination was carried out at the intermediate temperature for an interval of time, followed by raising the temperature (slow heating rate) to the final calcination temperature below 600° C. where the zeolite was calcined. The stepwise calcination procedure of the zeolite catalyst with MTT structure resulted in the removal of the organic template.

Example 6

Ion-Exchange Procedure

The sodium form of the zeolite catalyst having MTT structure, obtained from example 5, was transformed to proton form by repeated ion-exchange method using aqueous solutions of ammonium nitrate. After the ion-exchange procedure, the ammonium form of the zeolite was washed thoroughly with distilled water. The ammonium form of zeolite was dried at 100° C. for 10 h and it was transformed into proton form by calcination.

Example 7

Preparation of Zeolite Catalyst Having MTT Structure

Step a): Solution A was prepared by adding 8.9 g of sodium hydroxide to 392 g of distilled water and the mixture was stirred. 33.5 g of fumed silica was added to Solution A with a continuous stirring. After the addition of fumed silica, it was further stirred. This mixture is denoted as Solution B. Solution C was prepared by adding 3.9 g of aluminium sulphate ($Al_2(SO_4)_3.18H_2O$) to 49.2 g of distilled water and the mixture was further stirred. To this mixture, 17.9 g of pyrrolidine was added dropwise with vigorous stirring speed. After the addition of pyrrolidine the mixture was further stirred.

Solution C was slowly added to Solution B. After the addition of Solution C to Solution B the gel mixture was further stirred (gel ripening). To this gel mixture 8.0 g of sulphuric acid was added slowly. The prepared gel mixture was further stirred. (gel ripening).

Step b): The prepared gel mixture was put in a teflon cup inserted in a 300 ml steel autoclave. The autoclave was mounted over a shaft in an oven and the temperature of the oven was raised to 180° C. The synthesis was carried out under vigorous stirring for 48 hours at 180° C.

After completion of the synthesis, the autoclave was quenched. The product was mixed with distilled water, filtered and washed with on-line flowing distilled water.

The sample was left to dry over a filter paper. The crystalline product was separated from the filter paper and dried over a ceramic dish in an oven with airflow. The temperature and time of drying was 110° C. for 12 h, respectively. The product was calcinated for template removal.

Example 8

Ion-Exchange Procedure

The sodium form of the zeolite catalyst having MTT structure from example 7 was transformed to proton form by repeated ion-exchange method using aqueous solutions of ammonium nitrate. After the ion-exchange, the ammonium form of zeolite was washed thoroughly with distilled water. The ammonium form of zeolite was dried at 100° C. for 10 h and transformed into proton form by calcination. The obtained product was denoted "New catalyst B".

Example 9

Skeletal Isomerization with a Zeolite Catalyst Having MTT Structure

A catalyst having a MT structure (ZSM-23) was prepared according to the method described in Example 2 (New catalyst A). The activity was compared to those of the ferrierite type and ZSM-22 type catalysts in a fixed bed microreactor. Ferrierite A was a ferrierite catalyst without any carrier, ferrierite B was a ferrierite catalyst with alumina carrier and ferrierite C was a ferrierite catalyst with clay carrier. The feed contained 40 wt-% of n-hexane and 60 wt-% of n-hexenes. The tests were made at 225° C., 1 bar and with weight hourly space velocity (WHSV) of 20 l/h. Total run times were 48 hours. The yield of isohexenes (conversion of n-hexenes× selectivity to isohexenes) was determined from on-line GC-analysis of product samples.

Figure 3:
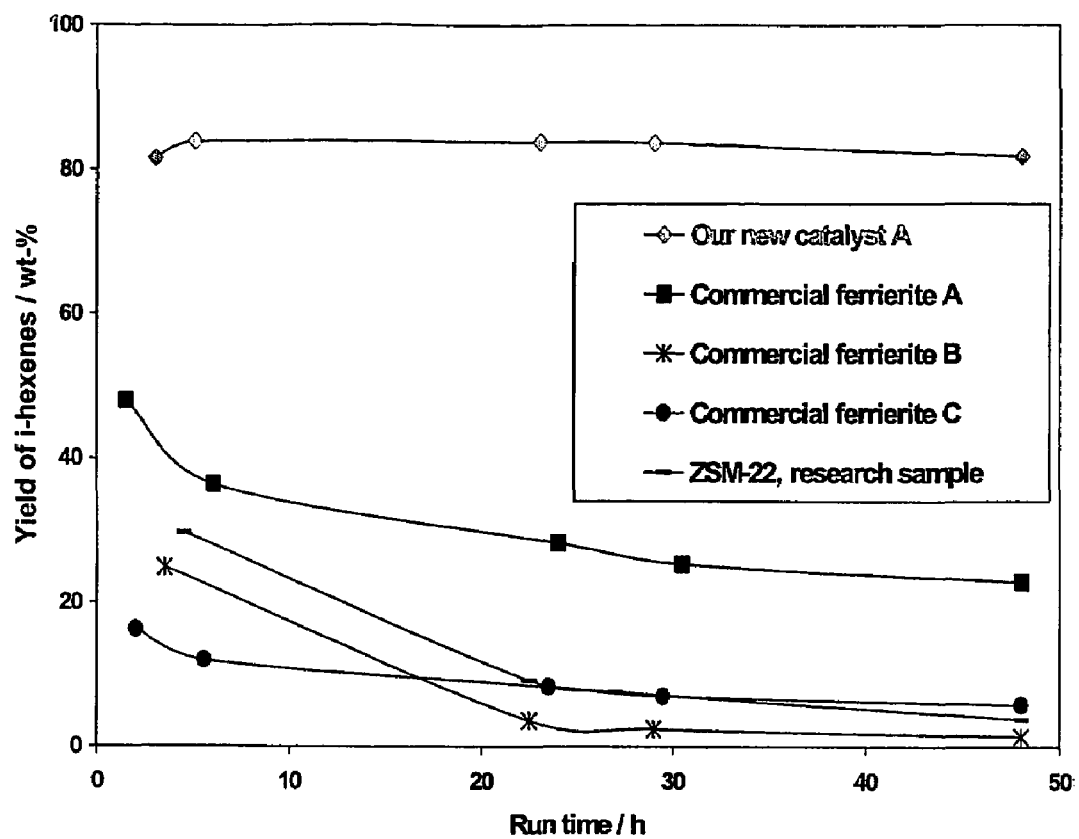

FIG. 3 shows the yields obtained with different catalysts as a function of time on stream. The yield of isohexenes was noticeably higher with the catalyst according to the invention having the MTT-structure than with ferrierite or ZSM-22 catalysts. In addition, no deactivation was observed with the catalyst of the invention.

Example 10

Skeletal Isomerization with a Zeolite Catalyst Having MTT Structure

The activity of a catalyst having a MTT structure, prepared according to the method described in Example 8 (New catalyst B), was compared to that of the ferrierite catalyst A with n-pentene feed. n-Pentenes were diluted with 50 wt-% n-pentane. The catalysts were tested in a microreactor at 225° C., 1 bar and with WHSV of 40 $h^{-1}$. Table 4 shows that the yield of isopentenes was higher with ZSM-23 (New catalyst B) than with the commercial ferrierite A after 25 hours on stream. The conversion of n-pentenes was noticeably higher with ZSM-23 (New catalyst B) than with the ferrierite A. The lower selectivity to isopentenes with the New catalyst B was related to the higher conversion level obtained.

TABLE 4

The activities with New catalyst B and with commercial ferrierite A after 25 hours on stream

|  | Conversion of n-pentenes/wt-% | Selectivity to i-pentenes/wt-% | Yield of i-pentenes/wt-% |
| --- | --- | --- | --- |
| New catalyst B | 64 | 84 | 54 |
| Commercial ferrierite A | 11 | 100 | 11 |

Example 11

Skeletal Isomerization of 1-butene with a Zeolite Catalyst Having MTT Structure

The activity of a catalyst having MTT-structure (New catalyst A), prepared according to Example 2, was tested in skeletal isomerization of 1-butene at 400° C. and under atmospheric pressure. The activity was compared to that of commercial ferrierite A and ZSM-22. n-Butene feed with WHSV of 44 h$^{-1}$ was used. The results in Table 5 show that at similar conversion level, the selectivity to isobutene was higher with the New catalyst A than with other catalysts.

TABLE 5

The selectivity to isobutene with the new catalyst A, with commercial ferrierite A and with ZSM-22

| | n-olefin/isoolefin ratio | Selectivity to isobutene/wt-% |
|---|---|---|
| New catalyst A | 1.5 | 74 |
| Commercial ferrierite A | 1.5 | 70 |
| ZSM-22, research sample | 1.5 | 66 |

Example 12

Skeletal Isomerization of n-hexenes

Figure 4:
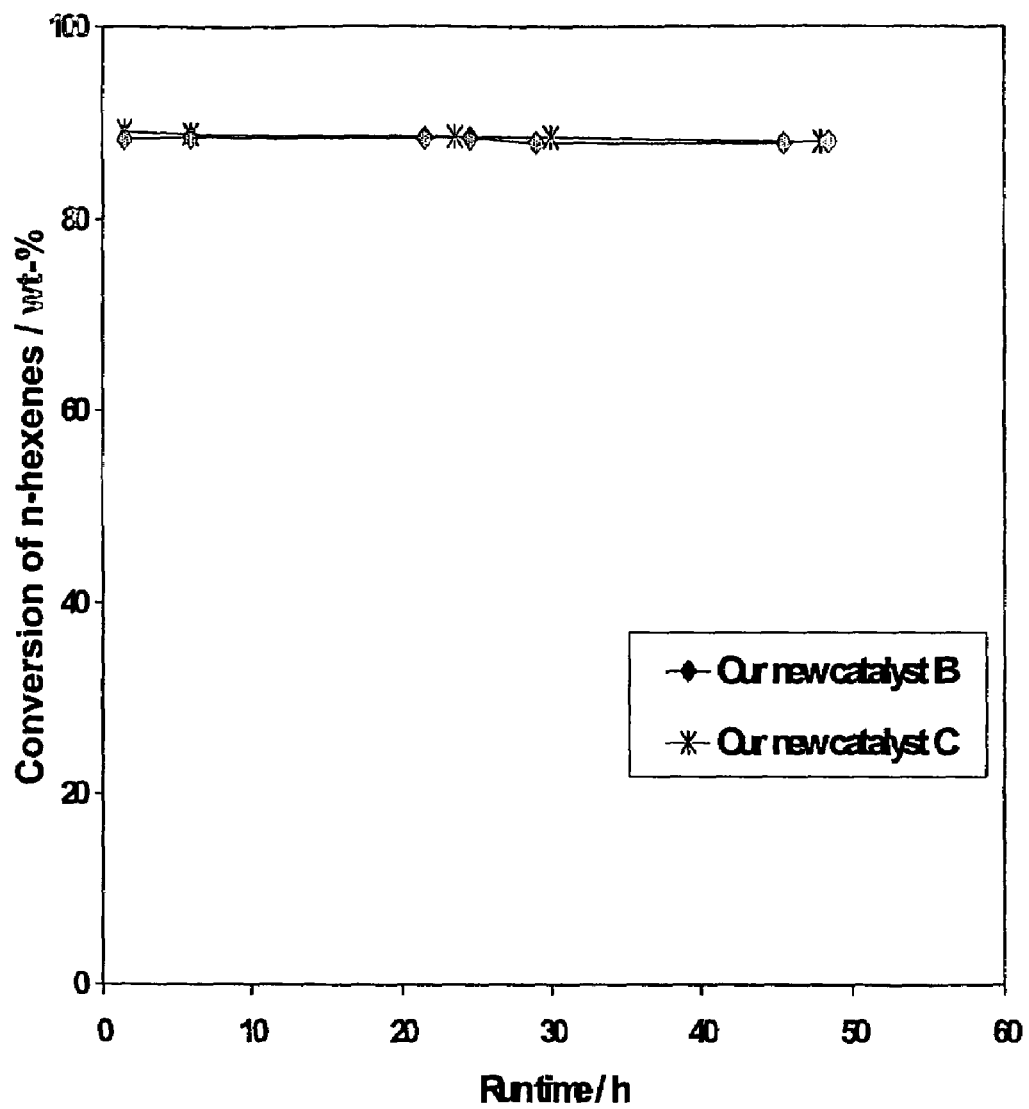

The activity of the catalyst prepared according to Example 8 (New catalyst B) was tested in skeletal isomerization of n-hexenes at 225° C. and 1 bar. In addition, the catalyst from Example 7 was calcined the same way as the catalyst in Example 8, but no ion-exchange was performed. This yielded New catalyst C. The activity of the New catalyst C was similar to that of the New catalyst B (FIG. 4). Ion exchange was, thus, not needed for the catalyst to be active under the used conditions.

Example 13 (Comparative Example)

Skeletal Isomerization of Hexene with a ZSM-23 Zeolite Catalyst

A ZSM-23 catalyst was prepared as instructed in U.S. Pat. No. 4,076,842. The activity of the ZSM-23 catalyst was studied in a fixed bed reactor. The test conditions were exactly the same as in Example 9. The obtained conversion of n-hexene was significantly low, being 1 wt-% or even lower.

REFERENCES 1. www.iza-online.org
2. On the role of small amines in zeolite synthesis, Rollmann, L. D., Schelenker, J. L. Lawton, S. L., Kennedy, C. L. Kennedy, G. J. Doren, D. J., J. Phys. Chem, B 103 (34) (1999) 7175.
3. Synthesis of high-silica zeolites with unidirectional medium pores systems using nitrogen free templates, Giordano, G., Di Renzo, F., Remoue, F., Fajula, F., Plee, D., Schulz, P., Stud. Surf. Sci. Cat. 84 (1994) 141.
4. The role of diquaternary cations as directing agents in zeolite synthesis, Moini, A., Schmitt, K. D., Valyocsik, E. W., Polomski, R. F., Stud. Surf. Sci. Cat. 84 (1994) 23.
5. Effect of synthesis time and mode of stirring on the physico-chemical and catalytic properties of ZSM-5 zeolite catalysts, Kumar, N., Nieminen, V., Demirkan, K, Salmi, T., Murzin, D. Yu., Laine, E., Appl. Catal. A: General 235 (2002) 113.
6. Deactivation of solid acid catalyst for butene skeletal isomerization: on the beneficial and harmful effects of carbonaceous deposits, van Donk, S., Bitter, J., de Jong, K., Appl. Catal. A: General 212 (2001) 97.

The invention claimed is:

1. A method for the manufacture of a zeolite catalyst, wherein the method comprises the following steps:

a) preparing a gel mixture capable of forming crystalline material using a gel ripening pre-treatment step which is carried out by adding one or more sources of alkali or alkaline earth metal (M) selected from the group consisting of sodium, potassium, magnesium, and calcium to water whereby Solution A is obtained, then adding one or more sources of an oxide of a tetravalent element (Y) selected from the group consisting of silicon and germanium to Solution A with continuous stirring whereby Solution B is obtained, then preparing Solution C by adding a source of an oxide of a trivalent element (X) selected from the group consisting of aluminum and gallium to water and adding to the obtained mixture a directing agent (R) selected from pyrrolidine and diethanolamine, adding the obtained Solution C to Solution B to obtain a gel mixture, stirring the gel mixture, then adding sulfuric acid to adjust the pH to a range of 8.5-13.5 and stirring the mixture, said mixture having a composition, in terms of molar ratios, within the following ranges:

| Molar ratio | Range |
|---|---|
| $YO_2/X_2O_3$ | 30 to 300 |
| $H_2O/YO_2$ | 20 to 100 |
| $OH^-/YO_2$ | 0.1 to 0.4 |
| $M/YO_2$ | 0.05 to 1.0 |
| $R/YO_2$ | 0.02 to 1.0 | b) carrying out hydrothermal synthesis wherein said mixture from step a) is maintained at a temperature from about 100° C. to about 250° C. under a dynamic mode of stirring until crystals of said material are formed, recovering the said material; and c) removing the directing agent (R) partly or totally with a stepwise calcination procedure wherein the temperature of the zeolite product obtained from step b) is raised to an intermediate temperature followed by raising the temperature to a final calcination temperature and obtaining a zeolite catalyst having a MTT structure with the following XRD pattern:

| D/n | Intensity I/I$_0$ |
|---|---|
| 10.8 | 42 |
| 9.95 | 16 |
| 7.77 | 37 |
| 4.507 | 90 |
| 4.241 | 79 |
| 3.88 | 100 |
| 3.704 | 80. |

2. The method according to claim 1 for the manufacture of a zeolite catalyst, wherein the source of an alkali or alkaline earth metal (M) is sodium hydroxide, potassium hydroxide or sodium carbonate, the source of an oxide of a trivalent element (X) is aluminium sulphate, hydrated aluminium hydroxides, aluminates, aluminium isoproxide or alumina and the source of an oxide of a tetravalent element (Y) is colloidal silica, solid silica, fumed silica or silica hydroxide.

3. The method according to claim 1 or 2 for the manufacture of a zeolite catalyst, wherein in step b) the hydrothermal synthesis is carried out at a temperature of 100-250° C., charging the gel mixture prepared in step a) into a reactor, and after the completion of the synthesis, the reactor is cooled, the product is isolated, washed with water, and dried.

4. The method according to claim 3 for the manufacture of a zeolite catalyst, wherein the intermediate temperature is 200-400° C. and the final calcination temperature is 400-600° C.

5. The method according to claim 3 for the manufacture of a zeolite catalyst, wherein in step b) the hydrothermal synthesis is carried out at a temperature of 120-220° C.

6. The method according to claim 3 for the manufacture of a zeolite catalyst, wherein the method additionally comprises replacing ions of the crystalline material, at least in part, by ion exchange with an ion or a mixture of ions selected from the group consisting of hydrogen and hydrogen precursors or metals.

7. The zeolite catalyst manufactured according to method of claim 1.

8. A zeolite catalyst according to claim 7, wherein the catalyst comprises 10-90wt-% of a carrier selected from alumina, silica or clay and combinations thereof.

9. A method for skeletal isomerization of olefins, wherein skeletal isomerization of a feed comprising olefinic hydrocarbons containing from 4 to 20 carbon atoms is carried out in the presence of a zeolite catalyst according to claim 7 or 8.

10. The method according to claim 9 for skeletal isomerization of olefins, wherein in the skeletal isomerization the temperature is 40-500° C. and the pressure is 0.1-5 MPa and the skeletal isomerization is carried out in a fixed bed reactor or in a fluidized bed reactor.

11. The method according to claim 9 for skeletal isomerization of olefins, wherein the feed is olefinic $C_4$ feed.

12. The method according to claim 9 for skeletal isomerization of olefins, wherein the feed is olefinic $C_5$ feed.

13. A method according to claim 9 for skeletal isomerization of olefins, wherein the feed is olefinic $C_6$ feed.

14. The method according to claim 9, wherein the feed comprises olefinic hydrocarbons containing 4 to 10 carbon atoms.

* * * * *